United States Patent [19]

Usher

[11] 4,347,847

[45] Sep. 7, 1982

[54] METHOD OF HERNIA REPAIR

[76] Inventor: Francis C. Usher, 2219 Richmond Ave., Houston, Tex. 77098

[21] Appl. No.: 157,146

[22] Filed: Jun. 6, 1980

[51] Int. Cl.$^3$ ............................................. A61B 17/04
[52] U.S. Cl. ................................. 128/334 R; 128/1 R
[58] Field of Search ............... 128/334 R, 334 C, 1 R; 3/1

[56] References Cited

FOREIGN PATENT DOCUMENTS 851720 10/1960 United Kingdom ............ 128/334 R

OTHER PUBLICATIONS

"Knitted Marlex Mesh" Surgery & Gyn. & Obs., 1963, p. 94.

*Primary Examiner*—Kyle L. Howell
*Assistant Examiner*—T. J. Wallen
*Attorney, Agent, or Firm*—Fulbright & Jaworski

[57] ABSTRACT

Disclosed is a continuously knitted tubular surgical mesh of monofilament threads free of water-leachable irritant impurities and physiologically inert even in the presence of infection, the threads being unattached at their points of crossing each other. Also disclosed are methods of using the surgical mesh in which the mesh is flattened thereby providing continuous knitted border edges on each side of the mesh, free of selvedge edges, which prevent unraveling or fraying of the border edges and at the same time avoid retaining any infection present by the border edges. Even though doubled, the tubular surgical mesh permits a greater porosity which allows substantially improved growth of tissues through it, it has greater stretch and flexibility than prior flat surgical meshes, and it avoids retaining infection or contamination by a selvedge edge. It also has increased tensile strength and improved flexural properties over prior flat meshes.

3 Claims, 11 Drawing Figures

METHOD OF HERNIA REPAIR

BACKGROUND OF THE INVENTION

A knitted mesh of polypropylene monofilament has been used for many years as a prosthesis for the repair of hernias and to close defects in the abdominal and chest walls.

The knitted mesh has been resistant to infection because of the open, porous construction of the weave and because it is made from monofilament rather than a braided yarn. Tissue grows to some extent through the mesh quite rapidly and it serves as an excellent reinforcement for the tissues.

The knitted mesh is frequently used in strips measuring one inch, two inches and ten inches in width. A selvedge edge, usually braided dacron, is provided on both edges of the strips to prevent unraveling or fraying of the mesh at the edges. This is very important because in hernia repair, sutures are placed through the mesh at the two borders to secure it to the tissues and frequently considerable tension is exerted on the border of the mesh. Selvedge edges cannot be placed on the two ends of the mesh strip because it has to be cut to size (crosswise) according to the size of the defect.

If the wound becomes infected, the selvedge edge retains infection because of the multiple filament yarn construction of the selvedge edge. This results in prolongation of the wound infection and frequently infected draining sinus tracts originating from the selvedge edge develope. This requires further surgery to remove the infected selvedge edge.

Examples of such knitted surgical mesh and methods of repairing body tissues with such surgical mesh are disclosed in my prior U.S. Pat. Nos. 3,054,406 and 3,124,136. In addition, Davol, Inc. has been marketing monofilament polypropylene mesh with selvedge edges under the Trademark "Davol/Usher's Marlex Mesh" as described above for many years.

It would be highly desirable to provide a knitted surgical mesh of greater porosity allowing better growth of tissue through it, one which is free of selvedge edges thereby avoiding retention of contamination or infection, and a mesh of greater strength and flexibility than prior surgical meshes. It is not possible to increase the porosity of prior flat surgical meshes because to provide a mesh of more open weave, the diameter of the threads would have to be increased which would make the mesh too stiff for practical use. Polypropylene mesh having a monofilament diameter of 6 mils and 68 stitches or courses to the inch is presently in use, and to make an open weave would require too large a monofilament diameter and thus provide too stiff a mesh.

SUMMARY OF THE INVENTION

The present invention is directed to a surgical mesh which is knitted in continuous tubular shape, free of selvedge edges, which in use is flattened and the mesh is sutured through the continuous border edges to the tissue, such as for the repair of hernias and to close defects in the abdominal and chest walls.

The tubular surgical mesh can be of greater porosity thereby allowing better growth of tissue through it, even when doubled, and it has greater stretch and flexibility because of its greater porosity or open or loose weave than prior surgical meshes. It avoids contamination at its edges since there are no braided selvedge edges as in prior surgical meshes.

The mesh may be made of any suitable monofilament threads free of water-leachable irritant impurities and which are physiologically inert even in the presence of infection. Suitable materials are knitted or woven tubes of polypropylene, dacron, teflon, or polyethylene monofilament.

The method comprises repairing of hernias by suturing the tubular surgical mesh to the tissues in flattened form by suturing through its continuous border edges to tissue adjacent and bridging the hernial defect, the tubular surgical mesh having sufficient openings even when doubled to permit rapid tissue growth through it.

Accordingly, it is an object of the present invention to provide a surgical mesh knitted in continuous tubular shape, free of selvedge edges, which in use is flattened and the mesh is sutured through the continuous border edges to the tissue adjacent and bridging the hernial defect.

It is a further object of the present invention to provide a surgical mesh of greater porosity thereby promoting better growth of tissue through it than prior surgical meshes.

It is a further object of the present invention to provide such a surgical mesh which has greater strength and stretch than prior surgical meshes.

A further object of the present invention is a surgical mesh which is free of selvedge edges yet the edges of the mesh do not fray or unravel when sutured at its edges adjacent to and bridging the hernial defect.

A further object of the present invention is the provision of a continuously knitted tubular surgical mesh of monofilament threads being unattached at their points of crossing, which, in use, is flattened thereby providing continuous knitted border edges on each side of the mesh, thereby avoiding the use of selvedge edges to prevent unraveling or fraying of the border edges, and which thereby avoids retaining any infection or contamination along the selvedge edges.

Other and further features, objects and advantages are set forth throughout the specification and claims.

DESCRIPTION OF THE PREFERRED EMBODIMENTS

Figure 1:
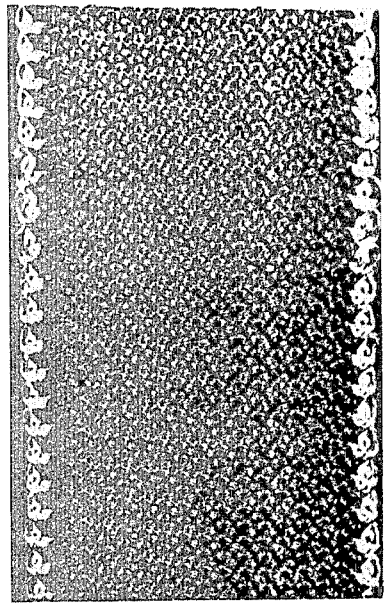
FIG. 1 is a photograph on a magnified scale (6×) of a portion of an actual surgical mesh strip of the prior art provided with selvedge edges.
Figure 1A:
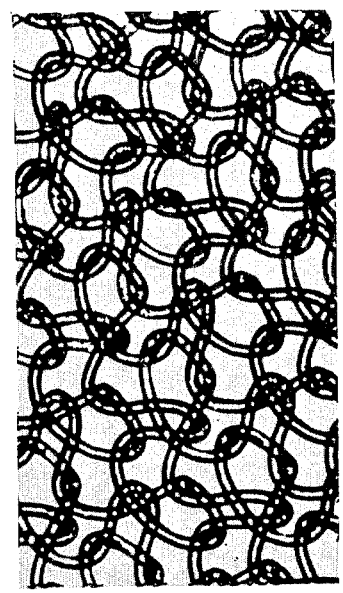
FIG. 1A is a further magnified (16×) of a portion of the mesh of FIG. 1.

Referring first to FIGS. 1 and 1A, a knitted surgical mesh of the prior art is illustrated. In order to prevent fraying or unraveling of the edges subject to tension by sutures in use, selvedge edges are provided on each side or border of the surgical mesh. This is very important because in hernia repair, sutures are placed through the mesh at the two borders to secure it to the tissues and frequently considerable tension is exerted on the border of the mesh. Selvedge edges cannot be placed on the two ends of the mesh strip because it has to be cut to size, that is cross-wise, according to the size of the defect or damaged tissue.

The selvedge edges are usually made of braided dacron and if the wound becomes infected, the selvedge edges retain infection because of the multiple filament yarn construction of the selvedge edge. This results in prolongation of the wound infection and frequently infected draining sinus tracts originating from the selvedge edge develope. This requires further surgery to remove the infected selvedge edge.

Figure 2:
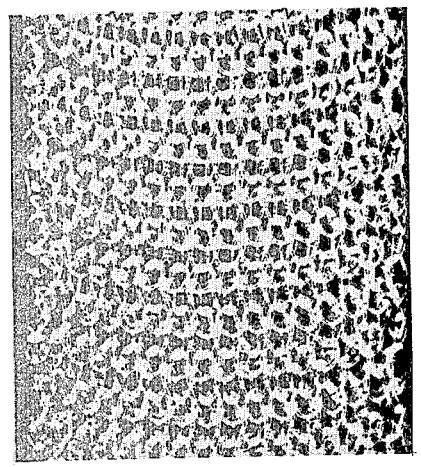
FIG. 2 is a magnified (6×) photograph of a portion of a tubular knitted surgical mesh according to the invention.
Figure 2A:
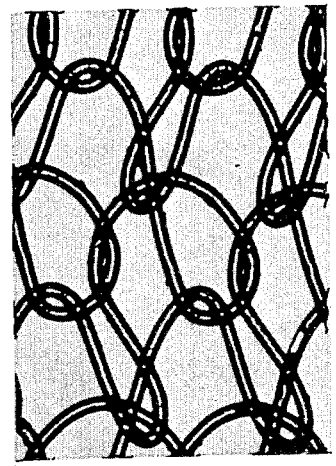
FIG. 2A is a further magnified (16×) photograph of the tubular surgical mesh of FIG. 2.

FIGS. 2 and 2A are photographs of continuously knitted tubular surgical mesh of the present invention. There is no selvedge edge provided along the border or edges of each side of the strip of mesh, the continuous knitted border edges being sufficient to prevent unraveling or fraying of the border edges as a result of suture tension and at the same time avoid retaining any infection present by the border edges such as in the case of strips of surgical mesh requiring selvedge edges as in the prior art and as illustrated in FIG. 1.

The surgical mesh is woven or knitted of monofilament threads free of water-leachable irritant impurites such as anti-oxidents and catalyst residues in order to prevent irritation and inflammation of animal tissue. In addition, the monofilament threads must be physiologically inert and non-irritating even in the presence of infection. The threads should be strong enough to withstand the conditions of use, for example, have a tensile strength of at least 50 psi.

The tubular surgical mesh is knitted in a continuous tubular shape with the threads being unattached to each other and nonmechanically joined at their points of contact or crossing which result in the mesh being highly pliable and having good stretch and flexibility.

A monofilament having a diameter of 5 to 15 mils and 10 to 20 stitches or courses per inch can be employed. A preferred tubular mesh is polypropylene having a diameter of 10 mils, 14 wales per inch, 15 stitches per inch, weighing 2.4 oz. per yard, and a 3 course atlas fully threaded Raschel chain notation 2/0-2/4-4/6-3/2; with no selvedge edge.

Any type of continuous knitting which would provide a tubular mesh as indicated above can be employed to make the surgical mesh. For example, double bar knit and double needle raschel fabric are satisfactory.

Any monofilament thread can be used which is free of water-leachable irritant impurities and is physiologically inert even in the presence of infection. At the present time polypropylene monofilament is preferred, but the surgical knitted tubular mesh can be woven from other monofilaments, such as dacron, teflon, or polyethylene monofilament.

For a further description of suitable monofilaments, their manufacture, and weaving or knitting of surgical mesh suitable for use in the present invention, reference is made to my prior U.S. Pat. Nos. 3,054,406 and 3,124,136. Accordingly, no further description is given or deemed necessary of the particular monofilament, its manufacture, or the knitting and the knitting parameters.

The tubular mesh may be knitted in a variety of sizes, that is widths of 1 inch, 1½ inch, 2 inch, 3 inch, 4 inch, 6 inch, 8 inch, 10 inch and larger, as desired and necessary.

The tubular mesh provides substantially increased porosity and hence substantially increased tissue growth through it and substantially decreases incidents of infection over the flat mesh and yet at the same time is flexible and has improved tensile strength and flex properties. For example, an 8 mil tubular mesh has 19 stitches to the inch which provides approximately 30% more porosity than a 6 mil flat mesh which has 68 stitches to the inch, and a 10 mil tubular mesh having from 10-15 stitches to the inch provides greater than 50% more porosity than a 6 mil flat mesh, thus substantially enhancing the growth of tissue through the tubular meshes.

The following Table I illustrates the results of tensile tests on polypropylene surgical mesh samples consisting of a flat 6 mil polypropylene monofilament having a dacron selvedge edge with tubular 8 and 10 mil polypropylene monofilaments.

TABLE I

| | TYPE | LENGTHWISE | | | |
| | | LENGTH | YARN | POUNDS | POUNDS |
| --- | --- | --- | --- | --- | --- |
| A-1 | Flat | 1" | 6 mil | 7.7 | 46 |
| A-2 | Flat | 2" | 6 mil | 5.4 | 59 |
| B-1 | Tubular | 1" | 8 mil | 144 | 144 |
| B-2 | Tubular | 2" | 8 mil | 250 | 277 |
| C-1 | Tubular | 1" | 10 mil | 220 | 220 |
| C-2 | Tubular | 2" | 10 mil | 294 | 294 |
| D-2 | Tubular | 2" | 10 mil | 237 | 260 |

| | TYPE | CROSSWISE | | | |
| | | WIDTH | YARN | POUNDS | POUNDS |
| --- | --- | --- | --- | --- | --- |
| A-2 | Flat | 2" | 6 mil | 43 | 69 |
| B-2 | Tubular | 2" | 8 mil | 34 | 60 |
| C-2 | Tubular | 2" | 10 mil | 29 | 66 |
| D-2 | Tubular | 2" | 10 mil | 32 | 66.5 |

The tension property was determined as pounds pulled at first break and final break at a pulling speed of 2"/min. Testing was done on Instron Universal Test Machine.

In the foregoing Table I, it is the 2nd break that is of importance in use. The 1st break merely consists of a beginning of an unraveling. It is seen that in the Lengthwise tensile test results, the tubular mesh has a tensile strength considerably greater than that of the flat mesh.

In the Crosswise testing, the difference is not s great as the cut edge of the tubular mesh begins to unravel. In use, the tubular mesh is stitched along its folded and uncut portion, as described subsequently.

The following Table II sets forth the tension and flexural properties of polypropylene surgical mesh. The samples are coded the same as they are in Table I for comparison purposes.

TABLE II

TENSION AND FLEXURAL PROPERTIES ON POLYPROPYLENE SURGICAL MESH

| | Flat 6 mil A-1" | Flat 6 mil A-2" | Tub 8 mil B-1" | Tub 8 mil B-2" | Tub 10 mil C-1" | Tub 10 mil C-2" |
|---|---|---|---|---|---|---|
| Pounds at Break | | | | | | |
| Longitudinal | | | | | | |
| First Break | 8 | 5 | 144 | 254 | 220 | 267 |
| Final Break | 46 | 59 | 144 | 277 | 220 | 294 |
| Transverse | | | | | | |
| First Break | — | 45 | — | 19 | — | 217 |
| Final Break | — | 56 | — | 50 | — | 265 |
| Flexes to Failure | | 426,000* or 526,000 | | 1,100,000 | | 1,100,000 |
| RESAMPLES | | | | | | |
| Pounds at Break | | | | | | |
| Longitudinal | | | | | | |
| First Break | 7 | 28 | 79 | 210 | 151 | 193 |
| Final Break | 42 | 60 | 113 | 238 | 173 | 281 |
| Transverse | | | | | | |
| First Break | — | 43 | — | 34 | — | 29 |
| Final Break | — | 69 | — | 60 | — | 66 |

*Broke overnight - could have been 420,000 + 6,000 or 420,000 + 106,000.

The flexural property of the samples in Table II was determined as number of flex to break using an MIT Folding Endurance Tester with 1.5 kg load and bending arc of 235°.

From the foregoing Table II it is readily seen that the tubular mesh has substantially increased flexural properties over that of the flat mesh.

Figure 3:
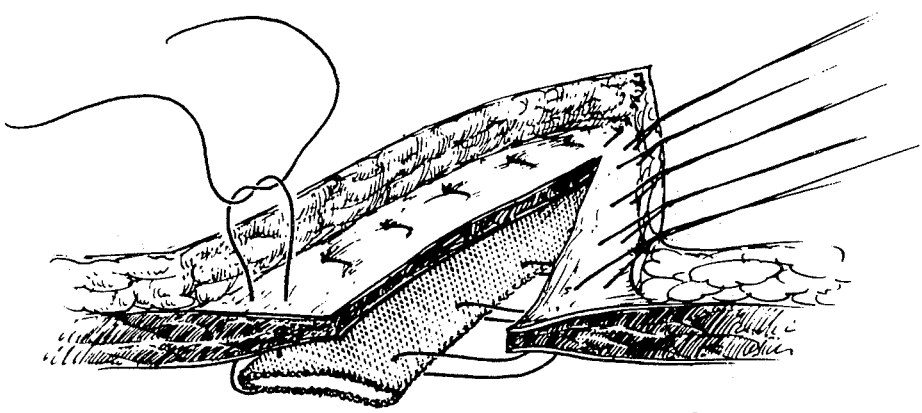
FIG. 3 is an example of the use of the tubular mesh of the present invention in the repair of an incisional hernia.
Figure 4:
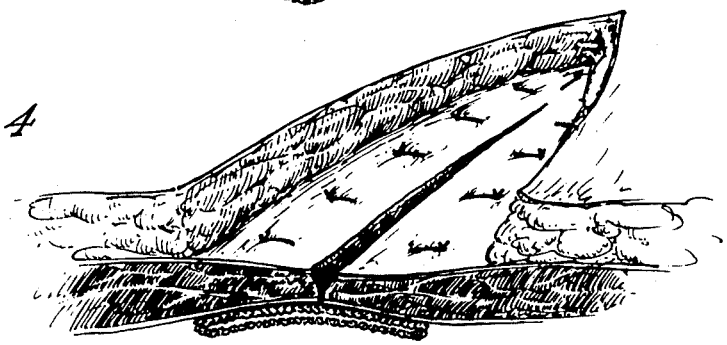
FIG. 4 is a view similar to that of FIG. 3 illustrating a further step in the use of tubular surgical mesh of the invention in the repair of an incisional hernia.
Figure 5:
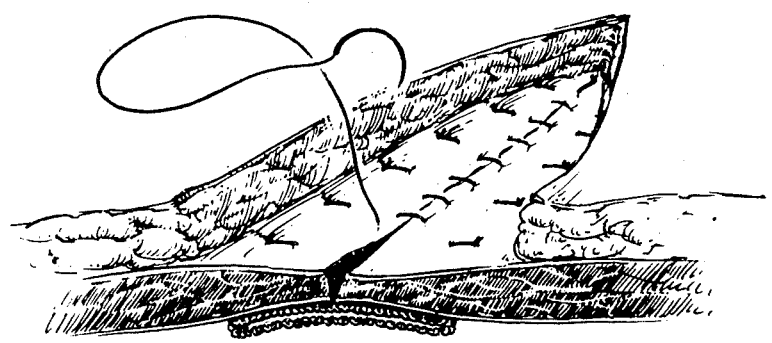
FIG. 5 is a view similar to that of FIG. 4 illustrating the closing of the anterior fascia completing the repair.

Referring now to FIGS. 3, 4 and 5, the use of the continuously knitted tubular surgical mesh of the present invention is illustrated in repairing incisional hernias.

In the repair of the incisional hernia, the hernial sac is dissected out and excised. The anterior fascia of the hernia ring is dissected free of subcutaneous fat for a distance of 1.5 inches circumferentially.

To serve as a retractor, a dinner plate, salad plate, or saucer (sterilized by autoclaving and not shown) is placed in an inverted position in the abdominal cavity to cover the bowel and omentum and to serve as a deflector for the mattress sutures to be placed through the musculofascial layer and peritoneum. The size of the plate is determined by the size of the defect. The largest plate that can be inserted through the hernial ring is selected. The inverted plate serves as an excellent weight retractor for the bowel and other viscera and makes the repair much easier. The plate, not shown, is removed just before pulling up and tying the sutures on the second side of the hernial ring. The tagged sutures on the second side of the repair must be left long at the time of placement to allow removal of the plate before closure of the second side.

As illustrated in FIG. 3, a two inch strip of a continuously knitted, tubular, surgical mesh of monofilament threads is flattened thereby providing continuous knitted border edges on each side of the mesh, free of selvedge edges, which is then sutured beneath the posterior aspect of the hernial ring, running the strip in the long axis of the defect and using suitable mattress sutures, such as no. 1 polypropylene monofilament. This is accomplished, as illustrated in FIG. 3, by first suturing the mesh below one edge, spacing the sutures 0.5 inch apart and 1.5 inches back from the edge of the hernial ring. The mattress suture is placed as a Lembert suture so that the closed loop lies at a right angle to the line of closure. This provides better spacing of the sutures and lessens the tendency of the mattress suture to cut through the tissue.

After all sutures have been placed and tied on one side, a mattress suture is placed at each end of the hernial defect (only one end being shown), passing through the ends of the 2 inch strip of tubular surgical mesh. These two sutures close the two ends of the defect.

As illustrated in FIGS. 3 and 4, mattress sutures are next placed on the opposite side of the defect to complete the closure. These sutures are placed and tagged with hemostats before typing because of limited accessibility. As best illustrated in FIG. 4, the sutures are placed 0.5 inch apart and 1.5 inches back from the hernial edge as on the opposing side.

To obtain even spacing of the sutures it is best to place them by "halving," that is, one at each end of the hernia defect, one in the middle, and so on until sufficient sutures have been placed to allow spacing of 0.5 inch between sutures. After all sutures have been placed and tagged, they are pulled up, held by the surgeons' assistant, and tied by the surgeon. It is best to have all the sutures pulled up at the same time, the assistant maintaining traction on them while the surgeon ties. In very large defects, it is desirable to have second and third assistants push in on each flank of the patient to achieve approximation of the hernial edges while the sutures are being tied.

Finally, and as illustrated in FIG. 5, a continuous suture is used to close the anterior fascia in the midline, over the mesh, such as with a suture of no. 0 polypropylene monofilament. If the mattress sutures have been correctly spaced (1.5 inches back from the hernial edge on each side), the musculofacial borders of the hernial ring should close without tension. This completes the repair.

Redundant skin and subcutaneous fat are then excised from both sides to allow a snug closure and eliminate dead space. Suction drains (closed drainage) are then placed subcutaneously to avoid any possible collection of blood postoperatively, the drains normally being left in place three to four days.

The foregoing is a preferred incisional hernia technique utilizing a knitted tubular surgical mesh of the invention. Other techniques, of course, can be used and in general, the tubular mesh can be used where all other meshes have been utilized in the past with improved results. This includes not only incisional but inguinal hernias and to close defects in the abdominal and chest walls.

In general, a 1½ inch tubular mesh is preferred for incisional hernias, using the technique described above, and a 1 inch tubular mesh is used for inguinal hernias. My article in *Surgery, Gynecology and Obstetrics,* September, 1970, vol. 131, 525–530 describes a technique for repairing incisional hernias utilizing the prior art flat mesh with selvedge edges which can be employed with the tubular surgical mesh of this invention.

Operations have been preformed upon three large incisional hernias in which the prior surgical mesh provided with selvedge edges as illustrated in FIGS. 1 and 1A, had been used with complete breakdown and reoccurrence. These were reoperated and the tubular mesh was used, as described above and the results have been excellent. No reoccurrences or wound complications in 60 such cases to the present time.

In addition, in another patient a one inch surgical mesh of the prior art as illustrated in FIGS. 1 and 1A, was removed because the wound became infected and drained for 2½ weeks. The mesh with the selvedge edges was removed and the wound healed. A reoccurrence then developed because of the breakdown of the repair, and the inguinal hernia was repaired using a one inch tubular mesh according to the invention without problem and the patient was cured.

Figure 6:
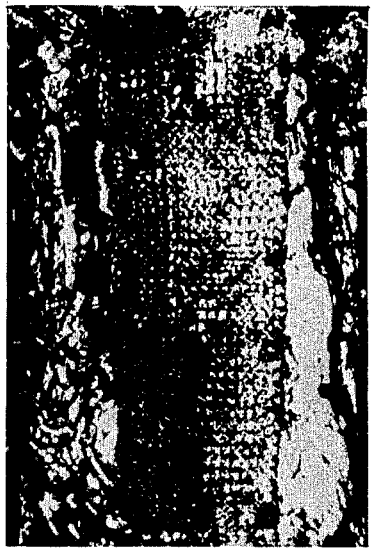
FIG. 6 is a photograph of the use of the prior art surgical mesh of FIGS. 1 and 2 to repair an incisional hernia on the left side of a dog.

In the repair of hernias, such as incisional and inguinal hernias and defects in the abdominal and chest walls, it is important to promote growth of the tissue through the mesh to provide additional strength to the repaired area. Referring now to FIG. 6, which is a photograph of a dog with an incisional hernia on its left side having the surgical mesh of FIGS. 1 and 1A of the prior art sutured in place. The mesh was purposely infected and the hernia closed.

Figure 6A:
FIG. 6A is a photograph the same as that of FIG. 6 taken eighteen days later.
Figure 7:
FIG. 7 is a photograph of the use of the tubular surgical mesh of FIGS. 2 and 2A in the repair of an incisional hernia on the right side of a dog.
Figure 7A:
FIG. 7A is a photograph of the repaired incisional hernia illustrated in FIG. 7 taken eighteen days later and illustrating tissue growth completely through the surgical mesh.

The surgical mesh of the present invention as illustrated in FIGS. 2 and 2A was sutured in the left side of the dog, deliberately infected, and the incisional hernia closed. Eighteen days later the right and left sides were opened and, as illustrated in FIG. 7A, the tissue had grown completely through the tubular surgical mesh thereby providing good tissue growth and strength to the damaged area, and as illustrated in FIG. 6A, very little tissue had grown through the prior art mesh on the left side.

In short, the advantages of the tubular surgical mesh of the present invention are: (1) it is stronger in tension and flexure than the surgical mesh of the prior art because of its two layer open construction; (2) it is possible to provide a more open weave, more porous mesh than the surgical mesh of the prior art, which permits more rapid tissue growth through it and lessens the chance of potentiating infection; (3) it has no selvedge edge which potentiates infection; (4) it has much greater two way stretch than does the prior surgical mesh which is of tremendous aid to the surgeon technically in both incisional and inguinal hernias. There are no disadvantages of the tubular mesh compared to the prior surgical mesh of which the inventor is aware.

Accordingly, the present invention is well suited and adapted to attain the objects and ends and has the advantages and features as mentioned as well as others inherent therein.

While presently preferred embodiments have been given for the purpose of disclosure, changes can be made therein which are within the spirit of the invention as defined by the scope of the appended claims.

What is claimed is:

1. A method of repairing hernias and other defects of the abdominal and chest wall comprising, placing a tubular surgical mesh over the defect in flattened form to provide continuous border edges, the tubular surgical mesh being of a size sufficient to bridge the defect and to position the continuous border edges on tissue adjacent opposite sides of the defect free of selvedge edges, suturing through the mesh adjacent the continuous border edges to the tissue, the tubular surgical mesh being comprised of monofilament threads free of water-leachable irritant impurities and being physiologically inert even in the presence of infection, and having a tensile strength sufficient when doubled to withstand wound tension, the threads and the mesh having a diameter in the range of 5 to 15 mils, and the mesh having 10 to 20 stitches per inch and being knitted in a continuous tubular shape with the threads being unattached to each other at their points of crossing.

2. The method of claim 1 where, the threads of the tubular surgical mesh are polypropylene monofilament.

3. The method of claim 1 where, the threads of the tubular surgical mesh have a diameter of 8 to 10 mils, and the monofilament is polypropylene.

* * * * *

UNITED STATES PATENT OFFICE
CERTIFICATE OF CORRECTION

Patent No. 4,347,847          Dated September 7, 1982

Inventor(s) Francis C. Usher

It is certified that error appears in the above-identified patent and that said Letters Patent are hereby corrected as shown below:

Column 2, line 49, after "(16X)", add -- photograph --

Column 3, line 60, delete ";" and insert -- , --

Column 4, line 61, delete "s" and insert -- so --

Column 6, line 34, delete "typing" and insert -- tying --

Column 6, line 56, delete "musculofacial" and insert -- musculofascia --

Column 7, line 13, delete "preformed" and insert -- performed --

Signed and Sealed this

Twelfth Day of April 1983

[SEAL]

Attest:

Attesting Officer

GERALD J. MOSSINGHOFF

Commissioner of Patents and Trademarks